United States Patent [19]
Johnson, Jr. et al.

[11] Patent Number: 6,060,430
[45] Date of Patent: May 9, 2000

[54] METHODS AND COMPOSITIONS FOR ENHANCING HERBICIDAL ACTIVITY

[75] Inventors: David Hallock Johnson, Jr., St. Paul, Minn.; Joseph Guerino, Jr., Burlington County, Burlington Township, N.J.; Charles Ortlip, Jr., Levittown; Laura Sue Quakenbush, Holland, both of Pa.

[73] Assignee: American Cyanamid Company, Madison, N.J.

[21] Appl. No.: 09/183,558

[22] Filed: Oct. 30, 1998

Related U.S. Application Data

[60] Provisional application No. 60/063,915, Oct. 31, 1997.

[51] Int. Cl.⁷ ..................................................... A01N 43/40
[52] U.S. Cl. .............................................................. 504/130
[58] Field of Search ..................................... 504/118, 130

[56] References Cited

U.S. PATENT DOCUMENTS

| | | | |
|---|---|---|---|
| 4,816,060 | 3/1989 | Steller et al. | 71/92 |
| 5,030,271 | 7/1991 | Watkins et al. | 71/92 |
| 5,510,318 | 4/1996 | Patel et al. | 504/223 |

OTHER PUBLICATIONS

The Imidazolinone Herbicides, CRC Press Inc., p. 34 (1991).

D.W. Ladner, Pesticide Science, 29, 317–333 (1990).

S.S. Seefeldt, J.E. Jenson and E.P. Fuerst, Weed Technology, vol. 9, p. 218–227 (1995).

*Primary Examiner*—Jose' G. Dees
*Assistant Examiner*—Alton Pryor
*Attorney, Agent, or Firm*—John W. Hogan, Jr.

[57] ABSTRACT

There is provided a method for enhancing the control of monocotyledenous and dicotyledenous plant species comprising applying to said plant species a combination of optically active R-imidazolinone compounds. Also provided is a herbicidal composition comprising a combination of R-imidazolinone compounds.

10 Claims, No Drawings

METHODS AND COMPOSITIONS FOR ENHANCING HERBICIDAL ACTIVITY

This application claims the benefit of Provisional Application No. 60/063,915 filed Oct. 31, 1997.

BACKGROUND OF THE INVENTION

Imidazolinone compounds and their herbicidal use are described in U.S. Pat. No. 4,798,619. Combinations of racemic imidazolinone compounds and their synergistic herbicidal effect are described in U.S. Pat. No. 5,030,271. The R and S optical isomers of imidazolinone compounds and their relative individual herbicidal effect are described in *The Imidazolinone Herbicides*, CRC Press, Inc. (1991).

In view of the imidazolinone art, in general, one would expect the R isomer of an imidazolinone compound to have a herbicidal effect of approximately 1.5–1.8 times greater than that of the corresponding racemic imidazolinone compound. Therefore, to the extent the combination of R-imidazolinone compounds behave as the combination of racemic imidazolinone compounds, one would expect a combination of R-imidazolinone compounds to demonstrate about a 1.5–1.8 times greater herbicidal effect than the corresponding combination of racemic imidazolinone compounds.

SUMMARY OF THE INVENTION

It has now been found, that combinations of the optically active R isomers of imidazolinone compounds such as R-imazethapyr and R-imazapyr demonstrate a surprisingly enhanced herbicidal effect when compared to the herbicidal effect of the corresponding combination of racemic compounds, as well as when compared to the herbicidal effect of the individual optically active R-imidazolinone components.

The present invention provides a method for enhancing the control of undesirable monocotyledenous and dicotyledenous plant species which comprises applying to the foliage of said plants or to the soil or water in which the seeds, tubers or other propagating organs thereof are growing or to be grown an effective amount of a combination of the R isomer of an imidazolinone compound plus the R isomer of a second different imidazolinone compound such as a combination of R-imazethapyr plus R-imazapyr.

The present invention also provides a herbicidal composition which comprises an inert liquid or solid carrier and an effective amount of a combination of R-imidazolinone compounds, such as a combination of R-imazethapyr plus, R-imazapyr.

DETAILED DESCRIPTION OF THE INVENTION

A constant concern in crop production is how to efficiently control weed competition with responsible ecological practices. One effective tool currently available to agriculturalists is the imidazolinone family herbicides. These compounds offer a mode of action which targets an enzyme which is only present in plants. Therefore, they are non-harmful to all non-plant life such as humans, animals, birds, fish and the like. Further, imidazolinone herbicides are effective at relatively low application rates. However, since they have a broad spectrum of weed control, and therefore, a variety of application uses, a new means of lowering the use rates needed to control weeds and diminishing the environmental load of active ingredient is desirable.

Surprisingly, it has now been found that the application of a combination of the R-isomer of one imidazolinone, or the salt thereof, with the R-isomer of another different imidazolinone, or the salt thereof, provides enhanced control of undesirable monocotyledenous and dicotyledenous plant species. The combination of R-imidazolinone compounds, or their salts, may be applied to the foliage or the soil or water in which the seeds, tubers or other propagating organs of said plant species are growing or are to be grown, preferably to the foliage. Advantageously, combinations of R-imidazolinones such as R-imazethapyr plus R-imazapyr, or the salts thereof demonstrate increased maize selectivity, particularly imidazolinone resistant or imidazolinone tolerant maize selectivity.

As used in the specification and claims, the term R-imidazolinone designates the optical isomer of an imidazolinone Compound having the R configuration assigned to the asymmetric carbon in the imidazolinone ring which is substituted by a methyl and an isopropyl group, for example an imidazolinone compound having the structure of formula I

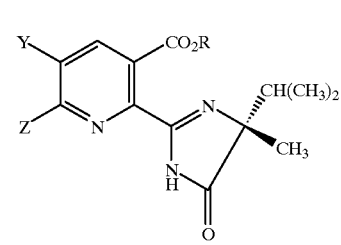

wherein R is H, or a cation; and

Y and Z are each independently H, $C_1$–$C_4$alkyl optionally substituted with $C_1$–$C_4$alkoxy or Y and Z may be taken together to represent —CH═CH—CH═CH—.

Examples of R-imidazolinone compounds of formula I useful in the method and composition of the invention include R-imazapyr, R-imazethapyr, R-imazaquin, R-imazamox, R-imazapic, and the like or a salt thereof, preferably R-imazethapyr and R-imazapyr or a salt thereof.

A cation, as used in the specification and claims, designates a positively charged moiety such as an alkali metal, an alkaline earth metal, ammonium, organic ammonium, manganese, copper, iron, zinc, cobalt, lead, silver, nickel and the like. Preferable cations are alkali metals, alkaline earth metals, ammonium or organic ammonium. Organic ammonium designates a positively charged nitrogen atom having one to four organic groups attached, such as alkyl, aryl or heteroaryl. The organic group may be cyclic or acyclic and may incorporate the positively charged nitrogen atom within the ring or without the ring. Preferable organic groups are alkyl groups such as isopropyl.

It is especially surprising that combinations comprising R-imatzethapyr plus R-imazapyr (or their salts) in a ratio of about 3 parts R-imazethapyr to one part R-imazapyr demonstrate a 2x–3x increase in weed control when compared to the corresponding combination of racemic imazethapyr plus racemic imazapyr (or their salts).

Advantageously, the method of invention may be used to enhance weed control at varied sites such as industrial, agricultural, recreational, ornamental and the like. In the instance of agricultural weed control, the method of invention is suitable for use in the presence of crop plant species and particularly in the presence of imidazolinone resistant or tolerant crop species such as legumes (e.g. peanuts or soybeans), IMI-CORN™, IMI™ canola, IMI™ wheat, IMI™ cotton, IMI™ rice and the like, especially IMI-CORN™.

The effective amount of the combination of R-imidazolinone compounds will vary according to the prevailing conditions such as weather, plant species, weed pressure, growth stage, mode of application, cultivation practice and the like. Generally effective amounts of a combination of R-imidazolinone compounds such as R-imazethapyr plus R-imazapyr may be about 0.003 kg/ha–0.250 kg/ha of R-imazethapyr plus about 0.001 kg/ha–0.083 kg/ha of R-imazapyr, preferably about 0.025–0.100 kg/ha of R-imazethapyr plus about 0.008–0.035 kg/ha of R-imazapyr.

In actual agricultural practice, the combination of R-imidazolinone compounds such as R-imazethapyr plus R-imazapyr may be applied simultaneously as a tank-mix partner or a co-formulant or sequentially as a separate application, preferably as a tank-mix partner or co-formulant. Therefore, the present invention also provides a herbicidal composition comprising an inert liquid or solid carrier and an effective amount of a combination of an R-imidazolinone compound plus a second different R-imidazolinone compound such as R-imazethapyr plus R-imazapyr or the salts thereof. Preferably, the R-imazethapyr and R-imazapyr, or their salts, are present in a ratio of about three parts of R-imazethapyr to one part R-imazapyr. Compositions of the invention include soluble granules, aqueous concentrates, dispersible granules, wettable powders, and the like, preferably soluble granules, aqueous concentrates or dispersible granules.

The agriculturally acceptable carrier may be a solid or liquid. Suitable solid carriers may be any inert carrier commonly used such as natural and synthetic clays and silicates, natural and synthetic resins, solid fertilizers and the like. Typical examples of a solid carrier include diatomaceous earth, talc, attapulgite, vermiculite, kaolinite, mica, calcium sulphate, silicon oxide, coumarone resin, polyvinyl chloride, styrene and the like. Similarly, suitable liquid carriers include water, glycols, alcohols, ketones, ethers, aromatic or araliphatic hydrocarbons, petroleum fractions, and the like, or mixtures thereof. Preferred carriers are water soluble carriers.

For a more clear understanding of the invention, specific examples thereof are set forth below. These examples are merely illustrative and are not to be understood as limiting the scope and underlying principles of the invention in any way. Indeed, various modifications of the invention, in addition to those shown and described herein, will become apparent to those skilled in the art from the following examples and foregoing description. Such modifications are also intended to fall within the scope of the appended claims.

EXAMPLE 1

Evaluation of the Enhanced Herbicidal Effect of the Combination of ohe R-Isomers of Imazethapyr and Imazapyr as Measured by Weed Control In this evaluation, plants are grown in standard greenhouse soil for 10–14 days until they are at the 2- to 4-leaf stage. Said plants are then sprayed with an aqueous solution of the test compounds which contains 0.25% of a non-ionic surfactant and 1% of a 28-0-0 liquid fertilizer. Each treatment is replicated 3 to 4 times. Approximately 3 weeks after treatment visual ratings are made using the rating scale shown below. The data are averaged and shown on Table I.

| Test Compound | Source |
| --- | --- |
| Imazethapyr | PURSUIT ®AS[1] |
| Imazapyr | ARSENAL ®AS[1] |
| Imazethapyr & Imazapyr | LIGHTNING ® AS[1] |
| R-imazethapyr | technical material[2] |
| R-imazapyr | technical material[2] |

[1]Manufactured by American Cyanamid Co.
[2]Formulated as an aqueous concentrate as described in U.S. 4,816,060.

| Rating Scale | |
| --- | --- |
| Rating | % Control (As Compared To Check) |
| 9 | 100 |
| 8 | 91–99 |
| 7 | 80–90 |
| 6 | 65–79 |
| 5 | 45–64 |
| 4 | 30–44 |
| 3 | 16–29 |
| 2 | 6–15 |
| 1 | 1–5 |
| 0 | No Effect |

| PLANT SPECIES | | |
| --- | --- | --- |
| Bayer Code | Scientific Name | Common Name |
| CHEAL | Chenopodium album, L. | Lambsquarters |
| AMBEL | Ambrosia artemisiifolia, L. | Ragweed |
| SETVI | Setaria viridis, (L) Beauv | Green Foxtail |
| ABUTH | Abutilon theophrasti, Medic. | Velvetleaf |

TABLE I

| | Rate | WEED CONTROL | | | |
| --- | --- | --- | --- | --- | --- |
| Compound | g/ha | CHEAL | AMBEL | SETVI | ABUTH |
| Imazethapyr | 4.00 | 2.5 | 2.5 | 3.5 | 2.5 |
| | 8.00 | 2.3 | 2.8 | 4.5 | 3.0 |
| | 16.00 | 3.5 | 4.0 | 4.3 | 4.0 |
| | 32.00 | 7.0 | 6.0 | 6.0 | 6.3 |
| | 64.00 | 8.0 | 6.5 | 7.5 | 6.3 |
| | 96.00 | 9.0 | 7.5 | 9.0 | 9.0 |
| | 128.00 | 9.0 | 8.8 | 9.0 | 9.0 |
| R-Imazetha- | 2.68 | 2.3 | 3.8 | 4.8 | 4.8 |

TABLE I-continued

| Compound | Rate g/ha | WEED CONTROL | | | |
|---|---|---|---|---|---|
| | | CHEAL | AMBEL | SETVI | ABUTH |
| pyr | 5.36 | 3.8 | 3.5 | 4.5 | 4.8 |
| | 10.72 | 4.0 | 3.0 | 5.5 | 4.8 |
| | 21.44 | 6.8 | 4.8 | 6.5 | 6.8 |
| | 42.88 | 7.0 | 6.5 | 7.5 | 7.0 |
| | 64.30 | 9.0 | 8.8 | 9.0 | 9.0 |
| | 85.76 | 9.0 | 9.0 | 9.0 | 9.0 |
| Imazapyr | 2.016 | 6.3 | 2.5 | 5.3 | 4.8 |
| | 4.00 | 8.0 | 4.0 | 6.8 | 6.3 |
| | 8.00 | 8.8 | 5.0 | 9.0 | 7.5 |
| | 16.00 | 9.0 | 7.0 | 9.0 | 8.5 |
| | 32.00 | 9.0 | 7.8 | 9.0 | 9.0 |
| | 48.00 | 9.0 | 8.8 | 9.0 | 9.0 |
| | 64.00 | 9.0 | 8.8 | 9.0 | 9.0 |
| R-Imazapyr | 1.34 | 7.3 | 1.5 | 6.0 | 4.3 |
| | 2.68 | 7.8 | 4.5 | 7.5 | 5.8 |
| | 5.36 | 8.3 | 5.0 | 8.0 | 7.3 |
| | 10.72 | 9.0 | 6.3 | 9.0 | 8.0 |
| | 21.44 | 9.0 | 7.5 | 9.0 | 9.0 |
| | 32.16 | 9.0 | 9.0 | 9.0 | 9.0 |
| | 42.88 | 9.0 | 8.5 | 9.0 | 9.0 |
| Imazethapyr plus Imazapyr | 3.02 + 1.0 | 4.3 | 2.5 | 3.0 | 4.5 |
| | 6.0 + 2.0 | 6.5 | 3.3 | 6.0 | 4.8 |
| | 12.0 + 4.0 | 7.5 | 5.5 | 7.3 | 6.8 |
| | 24.0 + 8.0 | 8.5 | 6.8 | 8.8 | 7.5 |
| | 48 + 16 | 8.8 | 7.5 | 9.0 | 8.8 |
| | 72 + 24 | 9.0 | 8.3 | 9.0 | 9.0 |
| | 96 + 32 | 9.0 | 9.0 | 9.0 | 9.0 |
| R-Imazetha-pyr plus R-Imazapyr | 2.01 + 0.67 | 5.3 | 4.3 | 5.5 | 5.5 |
| | 4.02 + 1.34 | 9.0 | 5.5 | 7.3 | 7.3 |
| | 8.04 + 2.68 | 8.8 | 6.3 | 8.8 | 7.5 |
| | 16.08 + 5.36 | 9.0 | 7.3 | 9.0 | 9.0 |
| | 32.16 + 10.72 | 9.0 | 8.0 | 9.0 | 9.0 |
| | 48.24 + 16.08 | 9.0 | 8.8 | 9.0 | 9.0 |
| | 64.32 + 21.44 | 9.0 | 9.0 | 9.0 | 9.0 |

EXAMPLE 2

Evaluation of the Enhanced Herbicidal Effect of the Combination of the R-Isomers of Imazethapyr and Imazapyr as Measured by Fresh Weight In this evaluation, plants are grown in standard greenhouse soil for 10–14 days until they are at the 2- to 4-leaf stage. Said plants are then sprayed with an aqueous solution of the test compounds which contains 0.25% of a non-ionic surfactant and 1% of a 28-0-0 liquid fertilizer. Test compounds used and the source thereof are the same as that described in Example 1. Each treatment is replicated 3 to 4 times. Approximately 3 weeks after treatment the plants are cut at the surface of the soil and weighed. The weights are reported as % of untreated check. The data are used to determine the rate at which a 50% plant growth inhibition as compared to the untreated check is obtained in grams per hectare. This rate is reported as the $I_{50}$ value. The $I_{50}$ values are calculated using the method described by Seefeldt, Jensen and Fuerst, Weed Technology, Vol. 9, p. 218–227 (1995). The $I_{50}$ values for the racemic test compounds and their corresponding R-isomers are compared and the ratio of $I_{50}$-racemic/$I_{50}$-R-isomer is recorded. The test results are shown in Table I, wherein the % fresh weight data are averaged.

| PLANT SPECIES | | |
|---|---|---|
| Bayer Code | Scientific Name | Common Name |
| IPOSS | *Ipomoea* spp. | Morningglory |
| AMBEL | *Ambrosia artemisiifolia*, L. | Ragweed |

TABLE II

| IMAZETHAPYR | | | R-IMAZETHAPYR | | | IMAZPAYR | | |
|---|---|---|---|---|---|---|---|---|
| Rate | % Fresh Wt. | | Rate | % Fresh Wt. | | Rate | % Fresh Wt. | |
| g/ha | IPOSS | AMBEL | g/ha | IPOSS | AMBEL | g/ha | IPOSS | AMBEL |
| 4.00 | 76 | 92 | 2.68 | 82 | 51 | 2.02 | 69 | 95 |
| 8.00 | 76 | 79 | 5.36 | 82 | 81 | 4.00 | 60 | 61 |
| 16.00 | 69 | 60 | 10.72 | 67 | 65 | 8.00 | 33 | 44 |
| 32.00 | 59 | 37 | 21.44 | 69 | 49 | 16.00 | 20 | 16 |
| 64.00 | 47 | 29 | 42.88 | 51 | 33 | 32.00 | 16 | 4 |
| 96.00 | 27 | 5 | 64.30 | 20 | 3 | 48.00 | 13 | 1 |
| 128.00 | 25 | 2 | 85.76 | 16 | 0 | 64.00 | 12 | 1 |
| $I_{50}$ (g/ha) | 35.0 | 22.0 | | 32.2 | 17.9 | | 3.21 | 6.16 |
| Ratio Racemic/R | IPOSS 1.09 | | | AMBEL 1.23 | | | IPOSS 1.51 | |

| R-IMAZAPYR | | | RACEMIC COMBINATION[1] | | | R-ISOMER COMBINATION[2] | | |
|---|---|---|---|---|---|---|---|---|
| Rate | % Fresh Wt. | | Rate | % Fresh Wt. | | Rate | % Fresh Wt. | |
| g/ha | IPOSS | AMBEL | g/ha | IPOSS | AMBEL | g/ha | IPOSS | AMBEL |
| | | | 3.0 1.0 | 69 | 103 | 2.01 0.67 | 70 | 84 |
| 1.34 | 76 | 111 | 6.0 | | | 4.02 | | |
| 2.68 | 57 | 76 | 2.0 12.0 | 63 | 92 | 1.34 8.04 | 68 | 57 |

TABLE II-continued

| | | | | | | | | |
|---|---|---|---|---|---|---|---|---|
| 5.36 | 33 | 56 | 4.0 | 64 | 53 | 2.68 | 45 | 36 |
| | | | 24.0 | | | 16.08 | | |
| 10.72 | 27 | 30 | 8.0 | 53 | 36 | 5.36 | 29 | 12 |
| | | | 48.0 | | | 32.16 | | |
| 21.44 | 17 | 7 | 16.0 | 37 | 21 | 10.72 | 20 | 6 |
| | | | 72.0 | | | 48.24 | | |
| 32.16 | 11 | 2 | 24.0 | 20 | 2 | 16.08 | 18 | 2 |
| | | | 96.0 | | | 64.32 | | |
| 42.88 | 13 | 4 | 32.0 | 18 | 0 | 21.44 | 18 | 3 |
| $Ig_{50}$ (g/ha) | 2.12 | 5.94 | | 15.2 | 20.5 | | 5.60 | 6.60 |
| Ratio Racemic/R | | AMBEL 1.01 | | IPOSS 2.71 | | | AMBEL 3.11 | |

[1]Imazethapyr plus imazapyr
[2]R-imazethapyr plus R-imazapyr

EXAMPLE 3

Field Evaluation of the Enhanced Herbicidal Effect of the Combination of the R-Isomers of Imazethapyr and Imazapyr In this evaluation, small field plots having an average size of 3M×25M are used. All treatments are applied using a backpack sprayer. Test applications are made 19 days after planting a variety of weed species and IMI™-tolerant maize crops. Commercially available formulations of the test compounds are used where available. All combination treatments are tank-mixed prior to application. All treatments contain 0.25% of a nonionic surfactant and 1.0% of a 28-0-0 liquid fertilizer. Approximately 8 weeks after treatment, the plants are evaluated visually and % weed control is recorded. The data obtained are shown in Table III. Three

PLANT SPECIES

| Bayer Code | Scientific Name | Common Name |
|---|---|---|
| BIDPI | *Bidens pilosa* L. | Beggartick, Hairy |
| CASOC | *Cassia occidentalis* | Coffee senna |
| HELAV | *Helianthus annuus*, L. | Sunflower |
| DEDTO | *Desmodium tortuosum, (SW)DC.* | Beggarweed, Florida |
| BOILF | *Borreria latifolia*, Schum. | Buttonweed, broadleaf |
| IAQGR | *Ipomoea grandifolia* | Morningglory |
| SETGE | *Setaria geniculata* (Lam.)P. Beauv. | Foxtail, knotroot |
| BRAPL | *Brachiaria plantaginea* (Link)Hitche. | Alexandergrass |
| DIGHO | *Digitaria horizontalis*, Wiild. | Crabgrass |
| CCHEC | *Cenchrus echinatus*, L. | Sandbur, Southern |
| PANMA | *Panicum maximum*, Jacq. | Guineagrass |

TABLE III

| TREATMENT | RATE g/ha | BIDPI | CASOC | HELAV | DEDTO | BOILF | IAQGR | SETGE | BRAPL | DIGHO | CCHEC | PANMA |
|---|---|---|---|---|---|---|---|---|---|---|---|---|
| Imazethapyr + Imazapyr | 12 + 4 | 10 | 20 | 10 | 0 | 20 | 10 | 10 | 5 | 30 | 10 | 10 |
| | 24 + 8 | 20 | 40 | 30 | 10 | 25 | 25 | 30 | 20 | 50 | 20 | 20 |
| | 48 + 16 | 70 | 60 | 70 | 40 | 50 | 50 | 60 | 40 | 75 | 70 | 70 |
| | 96 + 32 | 100 | 90 | 100 | 60 | 90 | 85 | 95 | 90 | 97 | 95 | 90 |
| R-Imazethapyr + R-Imazapyr | 8 + 2.7 | 20 | 40 | 25 | 10 | 40 | 30 | 20 | 10 | 30 | 10 | 20 |
| | 16 + 5.3 | 40 | 60 | 70 | 30 | 60 | 50 | 35 | 20 | 80 | 25 | 30 |
| | 24 + 8 | 90 | 75 | 80 | 50 | 70 | 70 | 90 | 90 | 90 | 90 | 70 |
| | 32 + 10.7 | 100 | 80 | 90 | 70 | 80 | 90 | 90 | 95 | 97 | 95 | 90 |
| | 64 + 21.3 | 100 | 95 | 100 | 90 | 95 | 100 | 100 | 100 | 100 | 100 | 100 | varieties of IMI™-tolerant maize were used in this evaluation. At 8 weeks after treatment, no injury, such as stunting or chlorosis, was observed for all 3 varieties of maize.

| Test Compound | Source |
|---|---|
| Imazethapyr | PURSUIT ®240 AS[1] |
| Imazapyr | ARSENAL ®240 AS[1] |
| R-imazethapyr | technical material[2] |
| R-imazapyr | technical material[2] |

[1]Manufactured by American Cyanamid Co.
[2]Formulated as an aqueous concentrate as described in U.S. 4,816,060.

EXAMPLE 4

Field Evaluation of the Enhanced Herbicidal Effect of the Combination of the R-Isomers of Imazethapyr and Imazapyr In this evaluation, small field plots (10M×2M) in which imidazolinone resistant (IR) corn plants have been sown are used. All treatments are applied, using a $CO_2$ sprayer, approximately 3 weeks after planting and are replicated 3 times. Commercially available formulations of test compounds are used where available. All treatments contain 0.25% of a nonionic surfactant and 1% of a 28-0-0 liquid fertilizer. At 27 and 62 days after treatment (DAT) visual observation of % weed control and % stunting are recorded.

The data obtained are shown in Table IV.

| Test Compound | Source |
|---|---|
| Imazethapyr + Imazapyr | PURSUIT ® 240 AS[1] + ARSENAL ® 240 AS[1] |
| R-imazethapyr + R-imazapyr | technical material[2] |

[1]Manufactured by American Cyanamid Co.
[2]Formulated as an aqueous concentrate as described in U.S. 4,816,060.

PLANT SPECIES

| Bayer Code | Scientific Name | Common Name |
|---|---|---|
| ANVCR | Anoda cristada, (L) Schlecht. | Spurred anoda |
| DIGSA | Digitaria, Sanguinalis, (LL) Scop. | Crabgrass |
| ELEIN | Eleusine indica, (L) Gaertn. | Goosegrass |
| POROL | Portulaca oleracea, (L) | Purslane |
| SORHAP | Sorghum halepense (L) Pers. | Johnsongrass, rhizome |

TABLE V

| | | % Weed Control | | | | % Stunting |
|---|---|---|---|---|---|---|
| | | DIGSA | | SORHAP | | |
| | Rate | (Days After Treatment) | | | | IR Corn |
| Compound | g/ha | 36 | 69 | 36 | 69 | 36 |
| Imazethapyr | 12 + 4 | 60 | 53 | 0 | 40 | 0 |
| plus | 24 + 8 | 93 | 77 | — | 68 | 0 |
| Imazapyr | 48 + 16 | 92 | 87 | 65 | 70 | 10 |
| | 60 + 20 | 99 | 92 | 93 | 70 | 3 |
| | 96 + 32 | 98 | 95 | 93 | 88 | 3 |
| R-Imazethapyr | 8 + 2.7 | 68 | 47 | 83 | 83 | 0 |
| plus | 16 + 5.35 | 92 | 77 | 80 | 83 | 0 |
| R-Imazapyr | 24 + 8 | 68 | 91 | 90 | 78 | 7 |
| | 32 + 10.7 | 99 | 99 | 95 | 95 | 7 |
| | 64 + 21.3 | 100 | 100 | 100 | 100 | 2 |

TABLE IV

| | | % WEED CONTROL | | | | | | | | | % Stunting |
|---|---|---|---|---|---|---|---|---|---|---|---|
| | | ANVCR | | DIGSA | | ELEIN | | POROL | | SORHAP | |
| | RATE | (Days after Treatment) | | | | | | | | | IR Corn |
| TREATMENT | g/ha | 27 | 62 | 27 | 62 | 27 | 62 | 27 | 62 | 27 | 62 | 27 |
| Imazethapyr + Imazapyr | 12 + 4 | 63 | 100 | 30 | 50 | 0 | 0 | 30 | 100 | 57 | 50 | 0 |
| | 24 + 8 | 92 | 100 | 78 | 70 | 37 | 0 | 65 | 100 | 83 | 60 | 0 |
| | 48 + 16 | 100 | 100 | 97 | 88 | 82 | 50 | 87 | 100 | 97 | 75 | 13 |
| | 60 + 20 | 100 | 100 | 88 | 85 | 37 | 70 | 100 | 100 | 93 | 90 | 2 |
| | 96 + 32 | 99 | 100 | 100 | 98 | 93 | 95 | 99 | 100 | 100 | 95 | 22 |
| R-Imazethapyr + R-Imazapyr | 8 + 2.7 | 77 | 100 | 53 | 60 | 0 | 0 | 68 | 100 | 57 | 50 | 7 |
| | 16 + 5.3 | 85 | 100 | 88 | 50 | 37 | 0 | 88 | 100 | 88 | 80 | 15 |
| | 24 + 8 | 98 | 100 | 97 | 95 | 63 | 50 | 99 | 100 | 99 | 95 | 8 |
| | 32 + 10.7 | 100 | 100 | 99 | 100 | 90 | 90 | 99 | 100 | 98 | 95 | 13 |
| | 64 + 21.3 | 100 | 100 | 100 | 100 | 91 | 98 | 100 | 100 | 100 | 98 | 13 |

EXAMPLE 5

Field Evaluation of the Enhanced Herbicidal Effect of the Combination of the R-Isomers of Imazethapyr and Imazapyr Using essentially the same procedure described in Example 4 and varying the location of the trial, a field evaluation of the combination of R-imazethapyr plus R-imazapyr is performed. Visual weed control evaluations are recorded at 36 and 69 days after treatment. Visual evaluation of % stunting of the IR corn crop is recorded at 36 days after treatment. The data obtained are shown in Table V.

PLANT SPECIES

| Bayer Code | Scientific Name | Common Name |
|---|---|---|
| DIGSA | Digitaria sanguinalis, (L.)Scop. | Crabgrass |
| SORHAP | Sorghum halepense (L.) Pers. | Johnsongrass, rhizome |

EXAMPLE 6

Postemergence Evaluation of the Enhanced Herbicidal Effect of the Combination of the R-Isomers of Imidazolinone Compounds In this evaluation, plants are grown in standard greenhouse soil for 10–14 days until they are at the 2- to 4-leaf stage. Said plants are then sprayed with aqueous test solutions prepared from formulated technical material containing 0.25% of a non-ionic surfactant. Each treatment is replicated 3 to 4 times. After spraying, the plants are placed on greenhouse benches and cared for in a manner commensurate with conventional greenhouse practice. Approximately 3 weeks after treatment the plants are visually evaluated for % weed control as compared to the untreated check. The data are averaged and shown in Table VI.

| \ | PLANT SPECIES | |
|---|---|---|
| Bayer Code | Scientific Name | Common Name |
| AMBEL | *Ambrosia artemisiifolia*, L. | Ragweed, common |
| PANMI | *Panicum miliaceum*, L. | Millet, wild proso |
| CYPRO | *Cyperus rotundus*, L. | Nutsedge, purple |
| IPOHE | *Ipomoea hederacea*, (L)Jacq. | Morningglory, ivyleaf |
| ABUTH | *Autilon theophrasti*, Medic. | Velvetleaf |
| DIGSA | *Digitaria sanguinalis*, (L)Scop | Crabgrass |
| ECHCG | *Echinochloa Crus-Galli*, (L) Beau | Barnyardgrass |
| CHEAL | *Chenopodium album*, L. | Lambsquarters |
| CASOB | *Senna obtusifolia*, (L.) | Sicklepod |

TABLE VI

Postemergence Herbicidal Evaluation

| TREATMENT | RATE g/ha | % WEED CONTROL | | | | | | |
|---|---|---|---|---|---|---|---|---|
| | | AMBEL | PANMI | CYPRO | IPOHE | ABUTH | DIGSA | CASOB |
| Imazaquin + Imazapyr | 1.5 + 0.5 | 3 | 0 | 3 | 3 | 3 | 8 | — |
| | 3 + 1 | 8 | 8 | 0 | 9 | 5 | 8 | — |
| | 6 + 2 | 24 | 20 | 3 | 19 | 18 | 10 | — |
| | 12 + 4 | 45 | 13 | 5 | 33 | 43 | 23 | — |
| | 8 + 24 | 76 | 40 | 30 | 50 | 80 | 63 | — |
| | 16 + 48 | 84 | 69 | 45 | 80 | 95 | 94 | — |
| | 32 + 96 | 95 | 95 | 64 | 89 | 100 | 100 | — |
| R-Imazaquin + R-Imazapyr | 1.5 + 0.5 | 13 | 6 | 0 | 0 | 6 | 5 | — |
| | 3 + 1 | 15 | 30 | 3 | 4 | 10 | 15 | — |
| | 6 + 2 | 38 | 13 | 10 | 36 | 29 | 18 | — |
| | 12 + 4 | 69 | 33 | 34 | 53 | 53 | 48 | — |
| | 8 + 24 | 85 | 78 | 48 | 79 | 96 | 88 | — |
| | 16 + 48 | 90 | 95 | 50 | 88 | 100 | 100 | — |
| | 32 + 96 | 99 | 100 | 65 | 93 | 100 | 100 | — |
| Imazamox + Imazapyr | 0.75 + 0.25 | 5 | 0 | 5 | 0 | 0 | 0 | — |
| | 1.5 + 0.5 | 14 | 6 | 0 | 3 | 16 | 0 | — |
| | 3 + 1 | 31 | 46 | 24 | 21 | 29 | 11 | — |
| | 6 + 2 | 58 | 28 | 20 | 29 | 54 | 31 | — |
| | 12 + 4 | 68 | 66 | 23 | 50 | 85 | 68 | — |
| | 24 + 8 | 78 | 83 | 45 | 71 | 100 | 93 | — |
| | 48 + 16 | 96 | 97 | 74 | 84 | 96 | 99 | — |
| R-Imazamox + R-Imazapyr | 0.75 + 0.25 | 11 | 23 | 3 | 6 | 5 | 5 | — |
| | 1.5 + 0.5 | 16 | 31 | 5 | 10 | 14 | 6 | — |
| | 3 + 1 | 28 | 14 | 14 | 16 | 35 | 15 | — |
| | 6 + 2 | 53 | 54 | 10 | 45 | 59 | 19 | — |
| | 12 + 4 | 78 | 65 | 30 | 60 | 91 | 73 | — |
| | 24 + 8 | 90 | 93 | 50 | 81 | 100 | 94 | — |
| | 48 + 16 | 97 | 98 | 73 | 91 | 100 | 100 | — |
| Imazapic + Imazapyr | 0.25 + 0.125 | 0 | 0 | 0 | 0 | — | — | 0 |
| | 0.5 + 0.25 | 0 | 1 | 1 | 0 | — | — | 0 |
| | 1 + 0.5 | 0 | 5 | 3 | 5 | — | — | 3 |
| | 2 + 1 | 11 | 48 | 5 | 20 | — | — | 6 |
| | 4 + 2 | 21 | 91 | 8 | 79 | — | — | 15 |
| | 8 + 4 | 73 | 100 | 20 | 81 | — | — | 49 |
| | 16 + 8 | 88 | 100 | 64 | 95 | — | — | 74 |
| R-Imazapic + R-Imazapyr | 0.25 + 0.125 | 0 | 0 | 0 | 0 | — | — | 0 |
| | 0.5 + 0.25 | 0 | 0 | 0 | 0 | — | — | 0 |
| | 1 + 0.5 | 5 | 46 | 3 | 33 | — | — | 3 |
| | 2 + 1 | 21 | 71 | 21 | 68 | — | — | 8 |
| | 4 + 2 | 48 | 100 | 5 | 73 | — | — | 54 |
| | 8 + 4 | 88 | 100 | 25 | 90 | — | — | 74 |
| | 16 + 8 | 86 | 100 | 61 | 94 | — | — | 83 |
| Imazethapyr + Imazapic | 0.75 + 0.25 | 0 | 0 | 0 | 0 | 0 | 0 | — |
| | 1.5 + 0.5 | 15 | 5 | 0 | 5 | 3 | 13 | — |
| | 3 + 1 | 19 | 18 | 5 | 19 | 13 | 14 | — |
| | 6 + 2 | 40 | 28 | 28 | 28 | 18 | 35 | — |
| | 12 + 4 | 60 | 46 | 30 | 38 | 55 | 68 | — |
| | 24 + 8 | 66 | 58 | 45 | 65 | 86 | 91 | — |
| | 48 + 16 | 90 | 93 | 75 | 80 | 98 | 98 | — |
| R-Imazethapyr + R-Imazapic | 0.75 + 0.25 | 10 | 0 | 10 | 0 | 3 | 5 | — |
| | 1.5 + 0.5 | 10 | 20 | 5 | 3 | 5 | 5 | — |

TABLE VI-continued

Postemergence Herbicidal Evaluation

| | | | | | | | | |
|---|---|---|---|---|---|---|---|---|
| | 3 + 1 | 20 | 8 | 5 | 13 | 18 | 16 | — |
| | 6 + 2 | 50 | 38 | 21 | 25 | 64 | 43 | — |
| | 12 + 4 | 53 | 80 | 28 | 53 | 73 | 65 | — |
| | 24 + 8 | 86 | 80 | 45 | 75 | 88 | 93 | — |
| | 48 + 16 | 91 | 98 | 89 | 96 | 89 | 99 | — |
| Imazaquin + Imazethapyr | 4 + 2 | 10 | 1 | 1 | 16 | — | — | 0 |
| | 8 + 4 | 34 | 20 | 14 | 15 | — | — | 1 |
| | 16 + 8 | 71 | 73 | 15 | 71 | — | — | 1 |
| | 32 + 16 | 81 | 90 | 53 | 75 | — | — | 29 |
| | 64 + 32 | 86 | 93 | 50 | 80 | — | — | 65 |
| R-Imazaquin + R-Imazethapyr | 4 + 2 | 24 | 26 | 6 | 8 | — | — | 3 |
| | 8 + 4 | 51 | 55 | 38 | 53 | — | — | 8 |
| | 16 + 8 | 69 | 58 | 16 | 70 | — | — | 8 |
| | 32 + 16 | 88 | 88 | 65 | 76 | — | — | 43 |
| | 64 + 32 | 95 | 96 | 71 | 83 | — | — | 75 |
| Imazaquin + Imazamox | 6 + 2 | 11 | 0 | 4 | 6 | 10 | 0 | — |
| | 12 + 4 | 24 | 3 | 8 | 10 | 21 | 6 | — |
| | 24 + 8 | 35 | 15 | 9 | 18 | 30 | 38 | — |
| | 48 + 16 | 71 | 45 | 23 | 39 | 71 | 84 | — |
| | 96 + 32 | 78 | 66 | 29 | 60 | 89 | 98 | — |
| R-Imazaquin + R-Imazamox | 6 + 2 | 13 | 3 | 9 | 8 | 14 | 6 | — |
| | 12 + 4 | 26 | 5 | 9 | 9 | 18 | 20 | — |
| | 24 + 8 | 64 | 19 | 18 | 24 | 33 | 50 | — |
| | 48 + 16 | 76 | 54 | 29 | 48 | 76 | 89 | — |
| | 96 + 32 | 85 | 79 | 65 | 65 | 80 | 94 | — |

| | | % WEED CONTROL | | | | | |
|---|---|---|---|---|---|---|---|
| TREATMENT | RATE g/ha | CHEAL | AM-BEL | A-BUTH | CASOB | ECHCG | IPOHE |
| Imazethapyr + Imazamox | 0.5 + 0.25 | 5 | 3 | 14 | 0 | 19 | 5 |
| | 1 + 0.5 | 28 | 9 | 19 | 0 | 58 | 36 |
| | 2 + 1 | 23 | 41 | 50 | 0 | 64 | 43 |
| | 4 + 2 | 39 | 63 | 63 | 3 | 71 | 63 |
| | 8 + 4 | 58 | 75 | 80 | 4 | 85 | 76 |
| | 16 + 8 | 65 | 76 | 80 | 30 | 99 | 73 |
| | 32 + 16 | 77 | 83 | 98 | 53 | 99 | 79 |
| R-Imazethapyr + R-Imazamox | 0.5 + 0.25 | 3 | 6 | 14 | 3 | 15 | 1 |
| | 1 + 0.5 | 31 | 41 | 18 | 0 | 59 | 40 |
| | 2 + 1 | 33 | 56 | 56 | 3 | 69 | 46 |
| | 4 + 2 | 48 | 71 | 70 | 4 | 79 | 66 |
| | 8 + 4 | 64 | 75 | 80 | 11 | 94 | 78 |
| | 16 + 8 | 61 | 75 | 79 | 34 | 100 | 75 |
| | 32 + 16 | 82 | 85 | 98 | 61 | 97 | 83 |

EXAMPLE 7

Preemergence Evaluation of the Enhanced Herbicidal Effect of the Combination of the R-Isomers of Imidazolinone Compounds In this evaluation, plant seeds are sown in pots containing a Sassafras sandy loam soil. Test solutions prepared as described in Example 6 are applied to the soil by spray application. After spraying, the plants are placed on greenhouse benches and cared for in a manner commensurate with convention al greenhouse practice. Each treatment was replicated 3–4, times. Approximately 3 weeks after treatment, visual evaluations of % weed control as compared to the untreated check are recorded. The data are averaged and shown in Table VII.

| PLANT SPECIES | | |
|---|---|---|
| Bayer Code | Scientific Name | Common Name |
| CYPRO | Cyperus rotundus, L. | Nutsedge, purple |
| PANMI | Panicum miliaceum, L. | Millet, wild proso |
| AMBEL | Ambrosia artemisiifolia, L. | Ragweed, common |
| DIGSA | Digitaria sanguinalis, (L)Scop | Crabgrass |
| ABUTH | Abutilon theophrasti, Medic. | Velvetleaf |
| IPOHE | Ipomoea hederacea, (L)Jacq. | Morningglory, ivyleaf |
| CASOB | Senna obtusifolia, L. Irwin and Barneby | Sicklepod |

TABLE VII

Preemergence Herbicidal Evaluation

| TREATMENT | RATE g/ha | % WEED CONTROL | | | | | | |
|---|---|---|---|---|---|---|---|---|
| | | CYPRO | PANMI | AMBEL | DIGSA | ABUTH | IPOHE | CASOB |
| Imazamox + Imazapyr | 0.75 + 0.25 | 1 | 3 | 1 | 5 | 21 | 1 | — |
| | 1.5 + 0.5 | 3 | 4 | 4 | 4 | 61 | 28 | — |
| | 3 + 1 | 6 | 9 | 5 | 23 | 83 | 46 | — |
| | 6 + 2 | 40 | 38 | 33 | 31 | 63 | 56 | — |
| | 12 + 4 | 44 | 59 | 60 | 45 | 99 | 75 | — |
| | 24 + 8 | 81 | 75 | 71 | 69 | 95 | 79 | — |
| | 48 + 16 | 94 | 89 | 79 | 93 | 95 | 84 | — |
| R-Imazamox + R-Imazapyr | 0.75 + 0.25 | 3 | 5 | 4 | 3 | 19 | 3 | — |
| | 1.5 + 0.5 | 5 | 1 | 6 | 6 | 23 | 8 | — |
| | 3 + 1 | 5 | 4 | 3 | 10 | 48 | 20 | — |
| | 6 + 2 | 21 | 39 | 18 | 45 | 85 | 64 | — |
| | 12 + 4 | 61 | 73 | 59 | 55 | 98 | 79 | — |
| | 24 + 8 | 81 | 76 | 68 | 79 | 100 | 81 | — |
| | 48 + 16 | 84 | 86 | 75 | 91 | 96 | 84 | — |
| Imazapic + Imazapyr | 1 + 0.5 | 0 | 26 | 3 | — | — | 50 | 0 |
| | 2 + 1 | 3 | 61 | 41 | — | — | 77 | 28 |
| | 4 + 2 | 54 | 73 | 45 | — | — | 81 | 35 |
| | 8 + 4 | 70 | 79 | 74 | — | — | 84 | 73 |
| | 16 + 8 | 83 | 81 | 82 | — | — | 91 | 93 |
| | 32 + 16 | 97 | 90 | 91 | — | — | 90 | 93 |
| R-Imazapic + R-Imazapyr | 1 + 0.5 | 0 | 31 | 11 | — | — | 52 | 0 |
| | 2 + 1 | 31 | 69 | 63 | — | — | 75 | 38 |
| | 4 + 2 | 66 | 78 | 68 | — | — | 84 | 65 |
| | 8 + 4 | 75 | 87 | 75 | — | — | 88 | 51 |
| | 16 + 8 | 96 | 92 | 93 | — | — | 90 | 98 |
| | 32 + 16 | 100 | 95 | 94 | — | — | 92 | 94 |
| Imazaquin + Imazapyr | 1.5 + 0.5 | 0 | 1 | 4 | 1 | 16 | 3 | — |
| | 3 + 1 | 5 | 9 | 9 | 15 | 38 | 18 | — |
| | 6 + 2 | 29 | 15 | 11 | 16 | 49 | 41 | — |
| | 12 + 4 | 40 | 21 | 46 | 48 | 73 | 54 | — |
| | 24 + 8 | 78 | 36 | 68 | 48 | 88 | 73 | — |
| | 48 + 16 | 74 | 63 | 75 | 71 | 99 | 81 | — |
| | 96 + 32 | 100 | 76 | 84 | 84 | 99 | 83 | — |
| R-Imazaquin + R-Imazapyr | 1.5 + 0.5 | 4 | 3 | 9 | 4 | 21 | 4 | — |
| | 3 + 1 | 10 | 0 | 11 | 11 | 35 | 1 | — |
| | 6 + 2 | 13 | 6 | 25 | 9 | 59 | 40 | — |
| | 12 + 4 | 29 | 30 | 65 | 43 | 78 | 69 | — |
| | 24 + 8 | 64 | 50 | 76 | 66 | 89 | 74 | — |
| | 48 + 16 | 84 | 69 | 75 | 71 | 89 | 80 | — |
| | 96 + 32 | 90 | 74 | 81 | 94 | 99 | 81 | — |
| Imazaquin + Imazapic | 2.25 + 0.5 | 3 | 3 | 6 | — | — | 8 | 10 |
| | 4.5 + 1 | 4 | 16 | 9 | — | — | 44 | 3 |
| | 9 + 2 | 34 | 58 | 59 | — | — | 76 | 14 |
| | 18 + 4 | 65 | 80 | 78 | — | — | 76 | 14 |
| | 36 + 8 | 71 | 96 | 91 | — | — | 94 | 80 |
| R-Imazaquin + R-Imazapic | 2.25 + 0.5 | 1 | 13 | 28 | — | — | 38 | 13 |
| | 4.5 + 1 | 11 | 45 | 48 | — | — | 70 | 25 |
| | 9 + 2 | 48 | 66 | 79 | — | — | 85 | 33 |
| | 18 + 4 | 83 | 87 | 89 | — | — | 91 | 70 |
| | 36 + 8 | 99 | 97 | 96 | — | — | 93 | 91 |
| Imazaquin + Imazamox | 3 + 1 | 0 | 3 | 0 | 3 | 0 | 3 | — |
| | 6 + 2 | 0 | 3 | 16 | 5 | 48 | 16 | — |
| | 12 + 4 | 0 | 6 | 46 | 45 | 59 | 50 | — |
| | 24 + 8 | 5 | 29 | 84 | 63 | 81 | 73 | — |
| | 48 + 16 | 28 | 61 | 91 | 71 | 94 | 85 | — |
| | 96 + 32 | 68 | 90 | 97 | 90 | 98 | 97 | — |
| R-Imazaquin + R-Imazamox | 3 + 1 | 0 | 3 | 14 | 4 | 40 | 10 | — |
| | 6 + 2 | 1 | 3 | 58 | 33 | 53 | 24 | — |
| | 12 + 4 | 6 | 53 | 65 | 53 | 73 | 71 | — |
| | 24 + 8 | 11 | 63 | 75 | 73 | 84 | 78 | — |
| | 48 + 16 | 59 | 78 | 92 | 84 | 95 | 94 | — |
| | 96 + 32 | 80 | 99 | 98 | 98 | 98 | 93 | — |
| Imazaquin + Imazethapyr | 4 + 2 | 0 | 6 | 9 | 16 | 33 | 0 | — |
| | 8 + 4 | 8 | 13 | 25 | 30 | 64 | 45 | — |
| | 16 + 8 | 46 | 59 | 74 | 60 | 80 | 78 | — |
| | 32 + 16 | 68 | 68 | 86 | 71 | 83 | 80 | — |
| | 64 + 32 | 84 | 81 | 93 | 86 | 93 | 91 | — |
| R-Imazaquin + R-Imazethapyr | 4 + 2 | 4 | 20 | 31 | 20 | 59 | 0 | — |
| | 8 + 4 | 28 | 51 | 71 | 60 | 68 | 0 | — |
| | 16 + 8 | 75 | 64 | 83 | 73 | 83 | 78 | — |
| | 32 + 16 | 86 | 84 | 95 | 80 | 93 | 91 | — |
| | 64 + 32 | 97 | 89 | 95 | 97 | 97 | 94 | — |
| Imazethapyr + Imazamox | 2 + 1 | 0 | 5 | 0 | 8 | 45 | 6 | — |

TABLE VII-continued

Preemergence Herbicidal Evaluation

| TREATMENT | RATE g/ha | % WEED CONTROL | | | | | | |
|---|---|---|---|---|---|---|---|---|
| | | CYPRO | PANMI | AMBEL | DIGSA | ABUTH | IPOHE | CASOB |
| | 4 + 2 | 14 | 34 | 8 | 20 | 63 | 44 | — |
| | 8 + 4 | 35 | 53 | 25 | 58 | 84 | 71 | — |
| | 16 + 8 | 63 | 76 | 70 | 74 | 94 | 89 | — |
| | 32 + 16 | 85 | 85 | 84 | 90 | 97 | 94 | — |
| R-Imazethapyr + R-Imazamox | 2 + 1 | 4 | 14 | 3 | 14 | 58 | 11 | — |
| | 4 + 2 | 18 | 25 | 23 | 40 | 71 | 35 | — |
| | 8 + 4 | 43 | 49 | 55 | 51 | 84 | 69 | — |
| | 16 + 8 | 80 | 76 | 79 | 76 | 93 | 88 | — |
| | 32 + 16 | 91 | 90 | 88 | 92 | 97 | 94 | — |

EXAMPLE 8

Evaluation of the Enhanced Herbicidal Effect of the Combination of the R-Isomers of Imidazolinone Compounds in Imidazolinone Tolerant (IT) Corn Field trials are conducted at various locations across the United States. The experimental design of each trial is a modified randomized complete block with a minimum 3 replications per treatment. Plot size is 10 to 12 feet wide and 30 to 40 feet long.

Planting time of IT corn varies depending on weather conditions and geographic region but is generally in late April to mid-June. Site preparation is consistent with local cultural practices and generally consists of 1 to 2 passes with a disc or field cultivator. IT Corn is sown in 30 inch rows.

Herbicides are applied with a tractor mounted sprayer equipped with a 10 to 12 foot boom, 8002 or 8003 flat fan nozzle tips, and delivering 20 gallons per acre (gpa) diluent volume pressurized at 35 to 45 psi. Postemergence herbicide application timings are based on weed and crop growth, and are generally at 1 to 3 inch weeds, or 5 to 8 inch corn.

Weed control in IT Corn trials is visually evaluated approximately 28 DAT (Table VIII)and 56 DAT (Table IX) and expressed as percent weed control (0 to 100% basis).

The data is averaged and shown in Tables VIII and Table IX.

TABLE VIII

| | Rate lbs/A | giant ragweed | Eclipta | pitted mgg | ivyleaf mgg | fall panicum | broadleaf signalgr | purple nutsedge | Texas panicum | vevlet leaf |
|---|---|---|---|---|---|---|---|---|---|---|
| imazapic/ imazapyr | 0.021 + .0042 | 69 | 75 | 80 | 95 | 97 | 90 | 67 | 72 | 99 |
| R-imazapic/ R-imazapyr | .014 + .003 | 76 | 77 | 92 | 98 | 99 | 90 | 65 | 70 | 99 |
| imazapic/ imazapyr | .032 + .0064 | 88 | 93 | 93 | 97 | 99 | 85 | 68 | 73 | 99 |
| R-imazapic/ R-imazapyr | .021 + .0042 | 76 | 97 | 87 | 100 | 98 | 86 | 50 | 53 | 99 |
| imazapic/ imazapyr | .047 + .0094 | 89 | 97 | 96 | 97 | 100 | 95 | 75 | 80 | 99 |
| R-imazapic/ R-imazapyr | .032 + .0064 | 87 | 95 | 95 | 98 | 100 | 93 | 73 | 75 | 99 |
| imazapic/ imazapyr | .094 + .019 | 86 | 96 | 97 | 97 | 100 | 96 | 80 | 80 | 99 |
| R-imazapic/ R-imazapyr | .064 + .013 | 96 | 98 | 97 | 96 | 100 | 96 | 80 | 83 | 99 |
| imazapic | 0.047 | 82 | 89 | 91 | 96 | 100 | 89 | 73 | 77 | 99 |
| R-imazapic | 0.032 | 84 | 90 | 89 | 96 | 99 | 80 | 60 | 62 | 99 |
| | Rate lbs/A | woolly cupgrass | sickle pod | Johnson grass | redroot pigweed | carpet weed | cult.d sunflower | giant foxtail | common waterhemp | common cocklebur |
| imazapic/ imazapyr | 0.021 + .0042 | 96 | 55 | 93 | 53 | 53 | 100 | 95 | 85 | 90 |
| R-imazapic/ R-imazapyr | .014 + .003 | 94 | 81 | 90 | 82 | 80 | 95 | 99 | 88 | 96 |
| imazapic/ imazapyr | .032 + .0064 | 93 | 82 | 82 | 85 | 85 | 100 | 99 | 87 | 93 |
| R-imazapic/ R-imazapyr | .021 + .0042 | 96 | 79 | 87 | 85 | 83 | 90 | 99 | 95 | 98 |
| imazapic/ imazapyr | .047 + .0094 | 97 | 91 | 97 | 83 | 83 | 100 | 99 | 93 | 97 |
| R-imazapic/ R-imazapyr | .032 + .0064 | 99 | 86 | 98 | 80 | 80 | 100 | 99 | 90 | 93 |
| imazapic/ imazapyr | .094 + .019 | 99 | 96 | 97 | 92 | 92 | 100 | 99 | 93 | 93 |

TABLE VIII-continued

|  | Rate lbs/A |  |  |  |  |  |  |  |  |
|---|---|---|---|---|---|---|---|---|---|
| R-imazapic/R-imazapyr | .064 + .013 | 99 | 96 | 95 | 95 | 95 | 100 | 100 | 80 | 93 |
| imazapic | 0.047 | 97 | 81 | 93 | 80 | 82 | 100 | 98 | 87 | 95 |
| R-imazapic | 0.032 | 97 | 80 | 82 | 83 | 87 | 100 | 99 | 83 | 90 |

TABLE IX

|  | Rate lbs/A | water hemp | fall panicum | green foxtail | Palmer amar | redroot pigweed | cockle bur | comm lambs | barnyard grass | hairy nightsh | giant foxt | shatter cane | giant rag |
|---|---|---|---|---|---|---|---|---|---|---|---|---|---|
| imazethapyr/imazapyr | .021 + .007 | 39 | 50 | 72 | 86 | 93 | 79 | 96 | 93 | 98 | 49 | 55 | 82 |
| R-imazethapyr/R-imazapyr | .014 + .005 | 55 | 82 | 93 | 93 | 97 | 79 | 93 | 92 | 98 | 55 | 95 | 78 |
| imazethapyr/imazapyr | .042 + .014 | 43 | 78 | 96 | 95 | 98 | 85 | 96 | 94 | 98 | 74 | 100 | 40 |
| R-imazethapyr/R-imazapyr | .028 + .009 | 58 | 99 | 99 | 95 | 98 | 91 | 95 | 97 | 97 | 76 | 100 | 37 |
| imazethapyr/imazapyr | .084 + .028 | 47 | 99 | 100 | 95 | 97 | 83 | 98 | 97 | 100 | 88 | 100 | 77 |
| R-imazethapyr/R-imazapyr | .056 + .018 | 69 | 100 | 100 | 93 | 97 | 93 | 98 | 98 | 100 | 91 | 100 | 74 |

What is claimed is:

1. A method for enhancing the control of undesirable monocotyledenous and dicotyledenous plant species which comprises applying to the foliage of said plant species or to the soil or water in which the seeds, tubers or other propagating organs thereof are growing or are to be grown an effective amount of a combination of at least two compounds selected from the group consisting of R-imazapyr or a salt thereof, R-imazethapyr or a salt thereof, R-imazaguin or a salt thereof, R-imazamox or a salt thereof, and R-imazapic or a salt thereof.

2. The method according to claim 1 wherein the combination of R-imazethapyr or R-imazapic or a salt thereof plus R-imazapyr or a salt thereof is applied to the foliage of said plant species.

3. The method according to claim 2 wherein said plant species are growing in the presence of maize.

4. The method according to claim 3 wherein the maize is imidazolinone tolerant or imidazolinone resistant maize.

5. A method for enhancing the control of undesirable monocotyledenous and dicotyledenous plant species which comprises applying to the foliage of said plant species or to the soil or water in which the seeds, tubers or other propagating organs thereof are growing or are to be grown an effective amount of a combination of R-imazethapyr or a salt thereof plus R-imazapyr, or a salt thereof wherein said R-imazethapyr or a salt thereof and R-imazapyr or a salt thereof are present in a ratio of three parts of R-imazethapyr to one part of R-imazapyr.

6. A method for enhancing the control of undesirable monocotyledenous and dicotyledenous plant species which comprises applying to the foliage of said plant species or to the soil or water in which the seeds, tubers or other propagating organs thereof are growing or are to be grown an effective amount of a combination of R-imazethapyr or a salt thereof plus R-imazapyr, or a salt thereof wherein the combination is applied at a rate of about 0.003 kg/ha–0.250 kg/ha of R-imazethapyr plus about 0.001 kg/ha–0.083 kg/ha of R-imazapyr.

7. The method according to claim 6 wherein the combination is applied at a rate of about 0.025 kg/ha–0.100 kg/ha of R-imazethapyr plus about 0.008 kg/ha–0.035 kg/ha of R-imazapyr.

8. A herbicidal composition which comprises an inert liquid or solid carrier and an effective amount of a combination of R-imazethapyr or R-imazapic plus-R-imazapyr, or the salts thereof.

9. A herbicidal composition which comprises an inert liquid or solid carrier and an effective amount of a combination of R-imazethapyr or R-imazapic plus-R-imazapyr, or the salts thereof wherein the R-imazethapyr or a salt thereof and R-imazapyr or a salt thereof are present in a ratio of about three parts R-imazethapyr to one part R-imazapyr.

10. The composition according to claim 8 wherein said carrier is water soluble.

* * * * *